(12) United States Patent
Kitamura

(10) Patent No.: US 7,037,717 B1
(45) Date of Patent: May 2, 2006

(54) CELL LINE AND SCREENING METHOD WITH THE USE OF THE SAME

(75) Inventor: Hidetomo Kitamura, Shizuoka-ken (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/380,372

(22) PCT Filed: Mar. 6, 1998

(86) PCT No.: PCT/JP98/00924

§ 371 (c)(1),
(2), (4) Date: Sep. 1, 1999

(87) PCT Pub. No.: WO98/39414

PCT Pub. Date: Sep. 11, 1998

(30) Foreign Application Priority Data

Mar. 7, 1997 (JP) .............................. 9-070556

(51) Int. Cl.
*C12N 5/00* (2006.01)

(52) U.S. Cl. ........................ 435/325; 435/366; 424/937
(58) Field of Classification Search ................ 435/325, 435/366; 424/937

See application file for complete search history.

(56) References Cited

U.S. PATENT DOCUMENTS 5,486,359 A * 1/1996 Caplan et al.
5,942,225 A * 8/1999 Bruder et al.

FOREIGN PATENT DOCUMENTS

WO WO 97/39104 10/1997
WO WO 98/04682 2/1998

OTHER PUBLICATIONS

Grigoriadis et al, J of Cell Biology, 106, Jun. 1988, 2139–2151.*

Gimble et al., Bone morphogenetic proteins inhibit adipocyte differentiation by bone marrow stromal cells. Journal of Cellular Biochemistry. 58:393–402 (1995).

Johnstone et al., In vitro chondrogenesis of bone marrow-–derived mesenchymal cells. Orthopedic Research Society, 65–11 (1996).

Pittenger et al., Oocytes and oogenesis. Osiris Therapeutics Inc.. 1772 (1996).

Aikawa et al., Establishment of bone morphogenetic protein 2 responsive chondrogenic cell line, Journal Of Bone And Mineral Research. 11(4)544–553 (1996).

Pietrangeli et al., Stromal cell lines which support lymphocyte growth: characterization, sensitivity to radiation and responsiveness to growth factors. Eur. J. Immunol., 18:863–872 (1988).

* cited by examiner

*Primary Examiner*—Leon B. Lankford, Jr.
(74) *Attorney, Agent, or Firm*—Browdy and Neimark

(57) ABSTRACT

An object of the present invention is to establish a clonal cell line of undifferentiated mesenchymal cells capable of differentiating into chondrocytes and adipocytes from a normal adult animal and to establish a screening method for cell differentiation-controlling materials. According to the present invention, cell lines capable of differentiating into chondrocytes and adipocytes, which are derived from normal adult animals; screening methods for cell differentiation-controlling materials using said cell lines; screening kits comprising said cell lines; cell differentiation-controlling materials obtained by said screening methods; and drugs containing said differentiation-controlling materials are provided.

6 Claims, 21 Drawing Sheets

Fig. 6

Type II collagen : 5'ACACAATCCATTGCGAACC3'. 5'AGATAGTTCCTGTCTCCGCC3'

Type X collagen : 5'CAGCTGGCATAGCAACTAAGG3'. 5'GTGGTTAGCACTGACAAGCG3'

Aggrecan core protein : 5'TGTTCAGTGGAACAGCAACC3'. 5'AGATTGTTCACTGACGTCCACC3'

PPAR-γ 2 : 5' CTGATGCACTGCCTATGAGC 3'  5' CATGAGGCCTGTGTTGTAGAGC 3'

*: $p<0.05$, **: $p<0.01$ vs. medium
(Dunnet's multiple comparison)

CELL LINE AND SCREENING METHOD WITH THE USE OF THE SAME

CROSS REFERENCE TO RELATED APPLICATION

The present application is the national stage under 35 U.S.C. 371 of PCT/JP98/00924, filed Mar. 6, 1998.

TECHNICAL FIELD

The present invention relates to novel cell lines capable of differentiating into chondrocytes and adipocytes, which are derived from normal adult animals, and novel in vitro screening methods capable of conveniently searching for materials which control differentiation from undifferentiated mesenchymal cells into chondrocytes and adipocytes using said cell lines.

BACKGROUND ART

Chondrocytes have been known to play important roles in the life of vertebrates, such as skeleton formation by endochondral ossification or smoothing of movements by articular cartilage. Damages in articular cartilages formed by chondrocytes are believed to be an important factor accelerating the progress of diseases such as osteoarthritis. Despite of the important in vivo roles of chondrocytes, the regulatory mechanism of differentiation from undifferentiated mesenchymal cells into chondrocytes has not been revealed at all.

On the other hand, adipocytes derived from undifferentiated mesenchymal cells like chondrocytes have been known to play an important role in the control of in vivo energy supply by accumulating lipid droplets in cytoplasms. It is needless to say that excessive accumulation of fats in adipocytes causes obesity and is taken as a hazardous factor for many diseases of adults. It is reported that the differentiation mechanism of adipocytes is controlled by an intranuclear receptor PPAR-$\gamma_2$ for a physiological ligand prostaglandin $J_2$, a transcription factor C/EBP-$\alpha$ or the like, but the mechanism has not been fully revealed.

As used herein, the undifferentiated mesenchymal cells generally mean those having a plurality of differentiation potencies, particularly mesoderm-derived cells having pluripotency. Specifically, mouse embryo-derived C3H10T1/2 (Cell, 17;771–779, 1979), rat fetus-derived RCJ3.1 (J. Cell. Bio., 106:2139–2151, 1988), rat neonate-derived ROB (Calcif. Tissue Int. 49 (3): 221–225, 1991) or the like have been known.

Cell lines having differentiation potency into chondrocytes and adipocytes seem to be useful for studying the regulatory mechanism of differentiation from such undifferentiated mesenchymal cells into chondrocytes and adipocytes, and include known cell lines derived from embryos (Cell, 17, 771 (1979)), tumors (J. Cell Biol. 130, 1461 (1995)), neonatal animals (J. Cell Biol. 106, 2139 (1988)) or the like, but any those derived normal adult animals have not been known at present.

If a clonal cell line of undifferentiated mesenchymal cells capable of differentiating into chondrocytes and adipocytes were established from a normal adult animal such as a normal adult mouse, it would provide a very useful means for studying the regulatory mechanism of differentiation of these cells in adult individuals.

DISCLOSURE OF THE INVENTION

An object of the present invention is to establish a clonal cell line of undifferentiated mesenchymal cells capable of differentiating into chondrocytes and adipocytes from a normal adult animal.

Another object of the present invention is to establish a method for screening for a cell differentiation-controlling material (for example, a material controlling differentiation into chondrocytes or adipocytes, a material controlling destruction of cartilage tissues or a material controlling calcification of chondrocytes), comprising using said cell line.

Still another object of the present invention is to provide a kit for screening for a cell differentiation-controlling material (for example, a material controlling differentiation into chondrocytes or adipocytes, a material controlling destruction of cartilage tissues or a material controlling calcification of chondrocytes), comprising said cell line.

Still another object of the present invention is to provide a cell differentiation-controlling material (for example, a material controlling differentiation into chondrocytes or adipocytes, a material controlling destruction of cartilage tissues or a material controlling calcification of chondrocytes), which is obtainable by a screening method using said cell line, and a drug containing said differentiation-controlling material.

As a result of careful studies to solve the above problems, the present inventors succeeded in establishing a clonal cell line from crural bones of a normal adult mouse. Detailed analysis of characteristics of this clonal cell line revealed that this cell line is capable of differentiating into chondrocytes and adipocytes, whereby the present invention was attained.

Tests of the reactivity of this cell line with cartilage-inducing materials such as human TGF-$\beta_1$ revealed that this cell line can be used to conveniently in vitro screen for cartilage-inducing materials.

It was also found that calcification of this cell line is inhibited by 1,25-dihydroxyvitamin $D_3$, revealing that this cell line can be used to conveniently in vitro screen for materials inhibiting calcification of cartilages.

It was also found that cartilage-like tissues formed by CL-1 cells in the presence of human TGF-$\beta_1$ are destroyed by inflammatory cytokines IL-1 or TNF-$\alpha$, revealing that this cell line can be used to conveniently in vitro screen for materials inhibiting such destruction of cartilages.

It was also found that 1,25-dihydroxyvitamin $D_3$ remarkably inhibits differentiation of this cell line into adipocytes, revealing that this cell line can be used to conveniently in vitro screen for materials inhibiting conversion into adipocytes.

Thus, according to a first aspect of the present invention, a cell line capable of differentiating into chondrocytes and adipocytes, which is derived from a normal adult animal is provided.

In one embodiment of said cell line, a cell line derived from a normal adult mouse is provided.

In one embodiment of said cell line, a cell line derived from undifferentiated mesenchymal cells is provided.

An example of said cell line is a strain bearing accession No. FERM BP-5823.

According to a second aspect of the present invention, a method for screening for a cell differentiation-controlling material (for example, a material controlling differentiation into chondrocytes or adipocytes, a material controlling destruction of cartilage tissues or a material controlling calcification of chondrocytes), comprising using a cell line of the present invention is provided.

In one embodiment of said screening method, the material screened for is a gene.

According to a third aspect of the present invention, a kit for screening for a cell differentiation-controlling material (for example, a material controlling differentiation into chondrocytes or adipocytes, a material controlling destruction of cartilage tissues or a material controlling calcification of chondrocytes), comprising a cell line of the present invention is provided.

According to a fourth aspect of the present invention, a cell differentiation-controlling material (for example, a material controlling differentiation into chondrocytes or adipocytes, a material controlling destruction of cartilage tissues or a material controlling calcification of chondrocytes), which is obtainable by a screening method using a cell line of the present invention, and a drug containing said differentiation-controlling material are provided. Specific examples of the drug containing the differentiation-controlling material according to the present invention include therapeutic agents for osteoarthritis, repairing agents for cartilage-containing tissues, antirheumatic agents, therapeutic agents for herniated disc and antiobesity agents.

BRIEF DESCRIPTION OF THE DRAWINGS

In FIG. 2, a: CL-1 cells cultured in a vehicle for 3 weeks post confluent; b: CL-1 cells cultured in the presence of 10 mM β-glycerophosphate for 3 weeks post confluent.

In FIG. 3, Lane a: total RNA extracted from subconfluent cultures; Lane b: total RNA extracted from one-week post-confluent cultures; Lane c: total RNA extracted from 2-week post-confluent cultures; and Lane d: total RNA extracted from 4-week post-confluent cultures.

In FIG. 4, Lane a: total RNA extracted from subconfluent cultures; Lane b: total RNA extracted from one-week post-confluent cultures; Lane c: total RNA extracted from 2-week post-confluent cultures; and Lane d: total RNA extracted from 4-week post-confluent cultures.

In FIG. 5, Lane a: total RNA extracted from subconfluent cultures; Lane b: total RNA extracted from one-week post-confluent cultures; Lane c: total RNA extracted from 2-week post-confluent cultures; and Lane d: total RNA extracted from 4-week post-confluent cultures.

FIG. 6 shows base sequences of the specific primers used for RT-PCR.

In FIG. 7, Lane a: total RNA extracted from subconfluent cultures; Lane b: total RNA extracted from one-week post-confluent cultures; Lane c: total RNA extracted from 2-week post-confluent cultures; and Lane d: total RNA extracted from 4-week post-confluent cultures.

In FIG. 13, a: CL-1 cells cultured in a vehicle for 3 weeks post confluent; b: CL-1 cells cultured in the presence of hTGF-$\beta_1$ (1.0 ng/ml) for 3 weeks post confluent; c: CL-1 cells cultured in the presence of hIGF-I (100 ng/ml) for 3 weeks post confluent.

In FIG. 19, a: CL-1 cells cultured in a vehicle for 3 weeks post confluent; b: CL-1 cells cultured in the presence of 1,25-dihydroxyvitamin $D_3$ ($10^{-7}$ M) for 3 weeks post confluent.

PREFERRED EMBODIMENT FOR CARRYING OUT THE INVENTION

Figure 1:
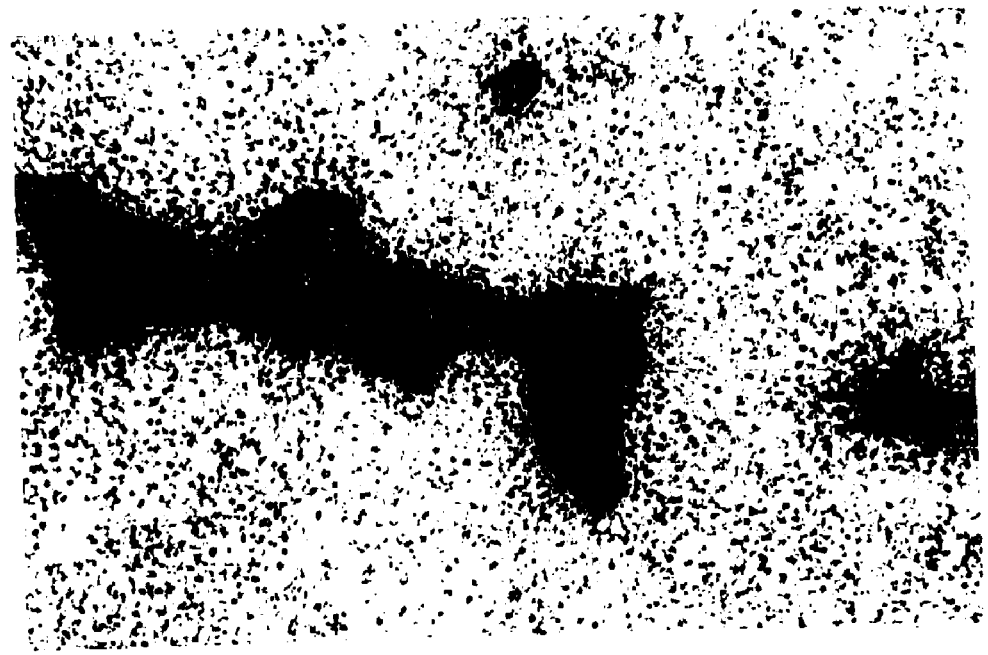
FIG. 1 is a photograph showing a double stained sample of 4-week cultures of CL-1 cells with Alcian blue (pH 1.0) and Oil red O.

A feature of cell lines of the present invention is that they are derived from normal adult animals.

As used herein, the term "normal adult" is used to exclude embryo-derived cells, tumor cells, neonate animal-derived cells or the like, and should be understood in a broad sense.

As used herein, the term "animal" means any animal such as mammals, reptiles, amphibians, fish, particularly mammals such as mouse, rat, human, monkey, hamster, preferably mouse.

Cell lines of the present invention can be established from various sites of said animals, such as crural bones, femoral bones, cranial bones, tracheae, auricles, noses, intervertebral disks, hearts, etc.

More specifically, a biological sample is extracted and cultured in an appropriate medium suitably supplemented with serum, antibiotics or the like for an appropriated period (for example, 9 to 15 days). Then, clonally growing cell colonies are isolated and continuously cultured. After further growth of cells, an appropriate number of passages (for example 10 to 12) are repeated. Finally, a clonal cell line can be established by cloning cells using an appropriate technique known to those skilled in the art for cloning cells such as limiting dilution.

Another feature of cell lines of the present invention is that they are capable of differentiating into chondrocytes and adipocytes.

Several tests can be used to determine whether or not cells have differentiated into chondrocytes. For example, cells cultured in a medium containing L-ascorbic acid can be stained with Alcian blue (pH 1.0) to test whether or not stained nodules are formed to determine whether or not they have differentiated into chondrocytes. Alcian blue used here is a dye which is a copper phthalocyanine derivative and can stain acid polysaccharides having carboxyl groups (polyanions) so that it is widely used in histochemistry to detect acid mucopolysaccharides (glycosaminoglycan) and distribution of sialic acid-containing glycoproteins in tissues. Alternatively, the uptake of $^{35}$S-labeled sulfuric acid into cell layers after cultivation in a medium containing $^{35}$S-labeled sulfuric acid (Calcif. Tissue Int. 19, 179–187, 1975) can be used to determine whether or not the cells have differentiated into chondrocytes, as commonly used to evaluate synthetic potency of cartilage matrix of primary cultures isolated from adult animals, particularly proteoglycan.

Alternatively, expression of type II collagen, type X collagen and aggrecan core protein in cells can be tested or ultrastructure within nodules of cells can be microscopically observed with, for example, a transmission electron microscope, to determine differentiation into chondrocytes.

Generally, a combination of a plurality of tests as described above is performed to determine differentiation into chondrocytes from overall results thereof. However, it should be understood that other tests than described above may also be performed to determine differentiation into chondrocytes, such as observation of metachromasia of nodules by toluidine blue staining.

Similarly, several tests can be used to determine differentiation into adipocytes. For example, intracytoplasmic accumulation of lipid droplets stained with Oil red O can be tested to determine differentiation into adipocytes. Alternatively, expression of PPAR-$\gamma_2$ may also be tested to determine differentiation into adipocytes.

A combination of a plurality of tests as described above can be performed to determine differentiation into adipocytes from overall results thereof, similarly to differentiation into chondrocytes. However, it should be understood that other tests than described above may also be performed to determine differentiation into adipocytes, such as intracytoplasmic accumulation of lipid droplets stained with Sudan III or expression of aP2 and adipsin.

Cell lines of the present invention can be cultured under any conditions that allow cells to survive or grow without dying. For example, cultivation temperature is typically 33 to 39° C., preferably 37° C. The culture medium used is α-MEM containing 3 to 10% (preferably 10%) of fetal bovine serum, preferably inactivated fetal bovine serum (fetal bovine serum having complements inactivated by heat treatment). Cultivation takes place under aeration with air containing 5% $CO_2$ at a constant humidity of 80 to 120% (preferably 100%).

Cell lines of the present invention can also be stored under any conditions, e.g. they can be cryopreserved at −80° C. or in liquid nitrogen as a suspension at a cell density of $10^2$ to $10^{10}$, preferably $10^4$ to $10^8$, more preferably $10^6$ cells/ml in a medium containing 10% glycerin or 10% dimethyl sulfoxide and 10% serum. Preferably, they are cryopreserved in liquid nitrogen as a suspension at a cell density of $10^6$ cells/ml in a medium containing 10% glycerin and 10% serum.

Cell lines stored as above can be grown again by, for example, rapidly thawing them in a water bath at 37° C., followed by stirring with a medium containing 10-fold amounts of 10% serum and centrifugation to harvest cells, which are then cultured in a medium containing 10% serum.

According to the second aspect of the present invention, a method for screening for a cell differentiation-controlling material (for example, a material controlling differentiation into chondrocytes or adipocytes, a material controlling destruction of cartilage tissues or a material controlling calcification of chondrocytes), comprising using a cell line of the present invention is provided.

As used herein, the "cell differentiation-controlling material" means any material participating in the control of cell differentiation, such as 1,25-dihydroxyvitamin $D_3$ and all trans-retinoic acid, which are known to induce differentiation of a human myeloid leukemia cell line HL-60 into macrophages and granulocytes, respectively. Cell lines of the present invention cover a material controlling differentiation into chondrocytes or adipocytes, a material controlling destruction of cartilage tissues or a material controlling calcification of chondrocytes. These materials include promoting factors of differentiation into chondrocytes such as human TGF-$\beta_1$ and human insulin-like growth factor-I, promoters of differentiation into adipocytes such as human insulin-like growth factor-I, inhibitors of differentiation into adipocytes such as human TGF-$\beta_1$ and 1,25-dihydroxyvitamin $D_3$, promoters of destruction of cartilage tissues such as IL-1 and TNF-α, and inhibiting factors of calcification of chondrocytes such as 1,25-dihydroxyvitamin $D_3$.

As used herein, the "material controlling differentiation into chondrocytes or adipocytes" means a material which induces or inhibits differentiation from undifferentiated cells such as undifferentiated mesenchymal cells into chondrocytes or adipocytes.

The material controlling differentiation into chondrocytes includes human transforming growth factor $\beta_1$ known to have cartilage-inducing ability and human insulin-like growth factor-I known to have an extracellular matrix production-promoting effect on chondrocytes.

The material controlling differentiation into adipocytes includes 1,25-dihydroxyvitamin $D_3$ known to inhibit conversion of a fat precursor cell line 3T3-L1 into fats and human insulin-like growth factor-I known to have a fat synthesis-promoting effect on adipocytes.

As used herein the "material controlling destruction of cartilage tissues" means a material which controls destruction of cartilage tissues formed by, for example, culturing cells capable of forming cartilages under certain conditions, particularly a material which promotes or inhibits destruction of said tissues.

The material promoting destruction of cartilage tissues includes inflammatory cytokines IL-1 or TNF-α.

As used herein, the "material controlling calcification of chondrocytes" means a material which promotes or inhibits calcification of chondrocytes, particularly a material which inhibits calcification of chondrocytes. Calcification of cells can be evaluated by, for example, determining the Ca content in cells. The material which inhibits calcification of chondrocytes includes 1,25-dihydroxyvitamin $D_3$.

As demonstrated in the examples below, cell lines of the present invention allow evaluation of the presence or absence of differentiation into chondrocytes and adipocytes, the extent of destruction of cartilage tissues and the extent of calcification of chondrocytes when using the materials mentioned above. Therefore, cell lines of the present invention clearly can be used to screen for a material controlling differentiation into chondrocytes or adipocytes, a material controlling destruction of cartilage tissues or a material controlling calcification of chondrocytes.

The material screened for includes not only biologically active materials per se having a differentiation control ability but also genes participating in differentiation control in some manner.

For example, cell lines of the present invention express mRNAs of type II collagen, type X collagen and aggrecan core protein as they differentiate into chondrocytes, as described above, and these mRNAs can be detected by a technique conventionally used by those skilled in the art to detect mRNA such as the RT-PCR method described in the examples below or the known TMA method (Transcription Mediated Amplification, JPA No. 500759/92). When the RT-PCR method is used, PCR primers specific to the sequence of a gene presumed to participate in differentiation into chondrocytes can be designed and used to perform the RT-PCR method, whereby the gene participating in differentiation into chondrocytes can be isolated.

These genes can also be isolated by the expression cloning method or the like. For example, a double-stranded cDNA library is prepared from mRNA extracted from cells of the present invention, and these cDNAs are integrated into an appropriate vector and transferred into an appropriate animal cell so that the cDNAs are expressed. A gene participating in differentiation into chondrocytes can be isolated by screening with an appropriate indication of differentiation into chondrocytes such as Alcian blue stainability.

Genes can also be isolated by the PCR method on the basis of the base sequence of a known gene which may be related or not to differentiation into chondrocytes. For example, a gene having a similar base sequence to that of a known gene can be amplified and isolated by performing PCR under appropriate conditions on a cDNA library prepared from mRNA extracted from cells of the present invention using primers-designed from the base sequence of the gene similar to the known gene.

Similarly, cell lines of the present invention express mRNA of PPAR-$\gamma_2$ known to participate in differentiation into adipocytes, and this mRNA can be detected by a technique conventionally used by those skilled in the art to detect mRNA such as the RT-PCR method or the known TMA method. When the RT-PCR method is used, PCR primers specific to the sequence of a gene presumed to participate in differentiation into adipocytes can be designed and used to perform the RT-PCR method, whereby the gene participating in differentiation into adipocytes can be isolated.

These genes can also be isolated by the expression cloning method or the like. For example, a double-stranded cDNA library is prepared from mRNA extracted from cells of the present invention, and these cDNAs are integrated into an appropriate vector and transferred into an appropriate animal cell so that the cDNAs are expressed. A gene participating in differentiation into adipocytes can be isolated by screening with an appropriate indication of differentiation into adipocytes such as intracytoplasmic accumulation of lipid droplets.

Genes can also be isolated by the PCR method on the basis of the base sequence of a known gene which may be related or not to differentiation into adipocytes. For example, a gene having a similar base sequence to that of a known gene can be amplified and isolated by performing PCR under appropriate conditions on a cDNA library prepared from mRNA extracted from cells of the present invention using primers designed from the base sequence of the gene similar to the known gene.

According to the present invention, a kit for screening for a material controlling differentiation into chondrocytes or adipocytes, a material controlling destruction of cartilage tissues or a material controlling calcification of chondrocytes, comprising a cell line of the present invention is also provided.

In the kit of the present invention, the cell line of the present invention is preferably maintained in a form which can readily restore a growable state. For example, it is cryopreserved in a medium containing 10% glycerin and 10% serum or maintained in a culture flask.

In addition to a cell line of the present invention, the present kit normally comprises a reagent for detecting changes of properties of said cell line which may be caused by the action of a material to be screened for and optionally specific reagent to be added into the medium during cultivation of the cell line.

In case of a kit for screening for a cartilage-inducing material or a kit for screening for a cartilage destruction-inhibiting material, for example, Alcian blue (pH 1.0), $^3$H-labeled glucosamine or $^{35}$S-labeled sulfuric acid can be used as a detection reagent.

In case of a kit for screening for an adipocyte differentiation-controlling material, Oil red O, Sudan III or a reagent for assaying triglyceride can be used as a detection reagent.

According to the present invention, a cell differentiation-controlling material (for example, a material controlling differentiation into chondrocytes or adipocytes, a material controlling destruction of cartilage tissues or a material controlling calcification of chondrocytes), which is obtainable by a screening method using a cell line of the present invention is also provided. The types of these materials are not specifically limited, but include any materials (including genes) screened by a screening method of the present invention.

These materials include those suitable as useful therapeutic agents in the field of repair or reconstruction of articular cartilages, ear or nose, maintenance of articular functions by inhibition of calcification of articular cartilages, inhibition of destruction of articular cartilages caused by inflammation of joint, or therapy of obesity or the like.

The following examples further illustrate the present invention without, however, limiting the same thereto.

EXAMPLES

Example 1

Establishment of a Clonal Cell Line

A cell line derived from normal adult mouse crural bones was established from proximal ends of crural bones of a 5-week old C57BL/6 mouse.

Namely, mouse crural bones were aseptically extracted, then proximal ends were excised and cultured for 9 days in αMEM (GIBCO) containing 10% inactivated serum (FBS), 100 U/ml penicillin and 100 μg/ml streptomycin on a 6-well plate (CORNING). After the medium was changed, cultivation was continued for further 4 days.

Then, clonally growing cell colonies were transferred to filter paper sections impregnated with 0.05% trypsin+0.02% EDTA (Sigma), and each section was cultured on a 24-well plate (CORNING). The medium was changed every 3 days. After cells were confirmed to reach confluent on day 7 from the start of cultivation of the filter paper sections, they were detached with Ca—Mg-free PBS and 0.05% trypsin+0.02% EDTA and subcultured onto a 60 mm dish (CORNING). The medium was changed every 3 days, and the cells were subcultured at a dilution factor of 4 on day 6 after the passage, and so forth to 16 passages. Cells of the 16th generation were cloned by limiting dilution to establish a clonal cell line CL-1.

Thus obtained cell line CL-1 was deposited on Feb. 18, 1997 at the Bioengineering Industry and Technology Research Institute of the Agency of Industrial Science and Technology, 1–3, Higashi 1-Chome, Tsukuba-city, Ibaraki-prefecture, Japan under accession No. FERM BP-5823.

Example 2

Characteristics of CL-1 Cells

Thus established CL-1 cells were screened for in vitro nodule formation ability and examined for the expression of mRNA of type II collagen, type X collagen, aggrecan core protein and PPAR-$\gamma_2$ using RT-PCR method, and submicrostructures were observed with a transmission electron microscope.

CL-1 cells were cultured for one month in a medium containing 50 μg/ml L-ascorbic acid (Wako Pure Chemical Industries). Then, the cells were fixed in 4% paraformaldehyde (pH 7.4), washed with 0.1 N hydrochloric acid, then stained with a 1% Alcian blue (EM Science) solution (pH 1.0) for one hour, extracted with 0.1 N hydrochloric acid and then observed with an optical microscope. As a result, nodules positively stained with Alcian blue (pH 1.0) appeared (see FIG. 1).

Figure 2:
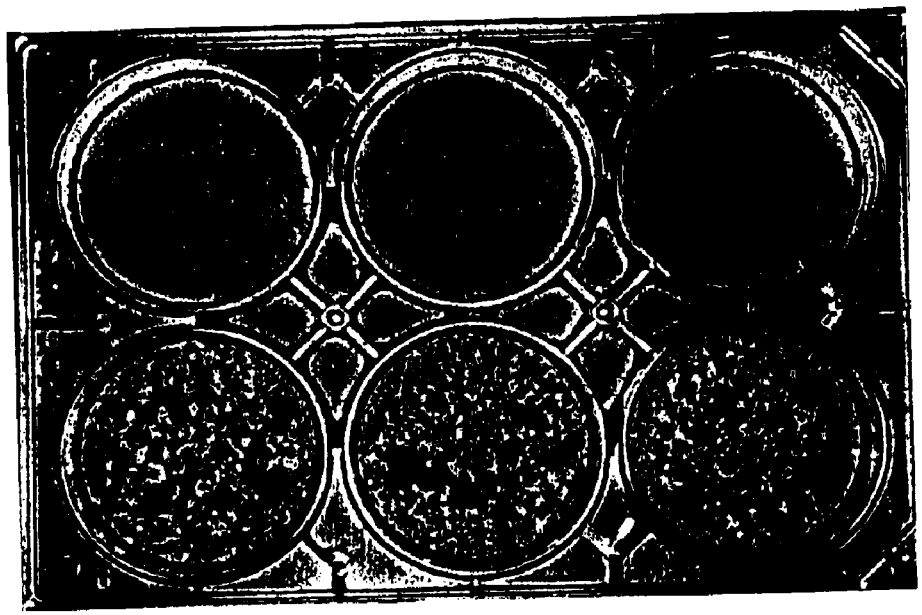
FIG. 2 is a photograph showing an Alizarin red S-stained sample of 4-week cultures of CL-1 cells in the presence of β-glycerophosphate.

CL-1 cells were similarly cultured in the medium supplemented with 10 mM β-glycerophosphate. Then, they were fixed in 4% paraformaldehyde (pH 7.4), washed with distilled water, then stained with a 1% Alizarin red S (Merck) solution for 5 minutes, washed with water and then observed with naked eyes and with an optical microscope. As a result, the nodules turned positive to Alizarin red S (see FIG. 2).

Intracytoplasmic accumulation of lipid droplets stained with Oil red O (0.5% in propylene glycol) was found at non-nodule forming sites (see FIG. 1).

The expression of mRNA of type II collagen, type X collagen and aggrecan core protein during nodule formation of CL-1 cells was analyzed by RT-PCR using an RNA PCR kit (Takara Shuzo) and primers having base sequences specific to them (see FIG. 6 and SEQUENCE LISTING). The sequences of the primers for detecting type II collagen in FIG. 6 are shown as SEQ ID NOS. 1 and 2; the sequences of the primers for detecting type X collagen in FIG. 6 are shown as SEQ ID NOS. 3 and 4; and the sequences of the primers for detecting aggrecan core protein in FIG. 6 are shown as SEQ ID NOS. 5 and 6. RT-PCR was performed by treating total RNA extracted from CL-1 with DNAse I (Takara Shuzo), then adding reagents according to the instructions attached to the kit for reverse transcription reaction, and subsequently performing PCR under the following conditions: one cycle at 94° C. for 1 minute, 40 cycles at 94° C. for 1 minute, 57° C. for 2 minutes and 72° C. for 3 minutes, and finally one cycle at 72° C. for 7 minutes, and cooling to 4° C.

Figure 3:
FIG. 3 is a photograph showing results of RT-PCR using type II collagen-specific primers.
Figure 4:
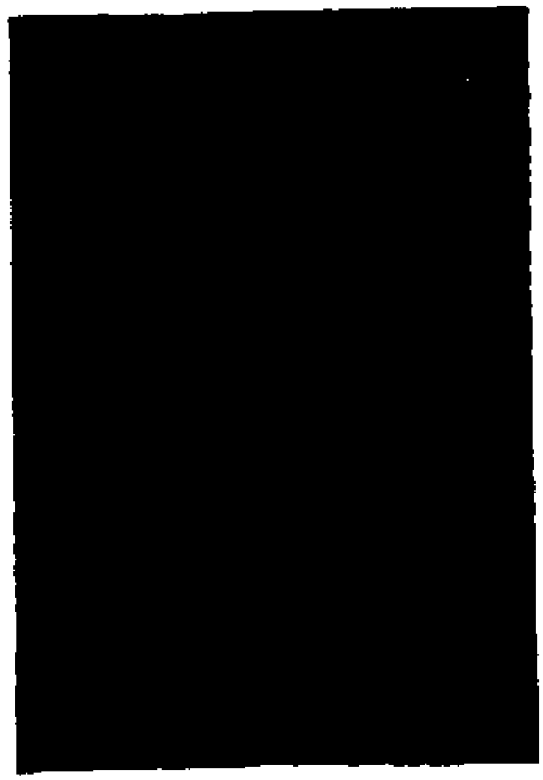
FIG. 4 is a photograph showing results of RT-PCR using type X collagen-specific primers.
Figure 5:
FIG. 5 is a photograph showing results of RT-PCR using aggrecan core protein-specific primers.

As a result, all the types of mRNA described above were found to be expressed (see FIGS. 3 to 5).

Figure 7:
FIG. 7 is a photograph showing results of RT-PCR using PPAR-$\gamma_2$-specific primers.

The expression of mRNA of PPAR-$\gamma_2$ was similarly analyzed by RT-PCR using primers (see FIG. 6 and SEQUENCE LISTING). The sequences of the primers for detecting PPAR-$\gamma_2$ in FIG. 6 are shown as SEQ ID NOS. 7 and 8. As a result, PPAR-$\gamma_2$ was also found to be expressed (see FIG. 7).

Figure 8:
FIG. 8 is a transmission electron microphotograph (4000× magnification) of the inside of nodules formed by CL-1 cells.

Observation of submicrostructures in the nodules of CL-1 cells with a transmission electron microscope revealed cell morphology and intercellular matrix structure similar to those of chondrocytes (see FIG. 8).

These results showed that CL-1 cells are mesenchymal cells capable of differentiating into chondrocytes and adipocytes.

In addition, CL-1 cells cultured for one month in the presence of γ-glycerophosphate formed Alizarin red S-positive nodules, revealing that cartilage-like cells derived from CL-1 cells can differentiate up to calcified cartilages corresponding to the final differentiation stage of cartilages.

Example 3

In vitro Evaluation of Cartilage-inducing Ability Using CL-1 Cells

Figure 9:
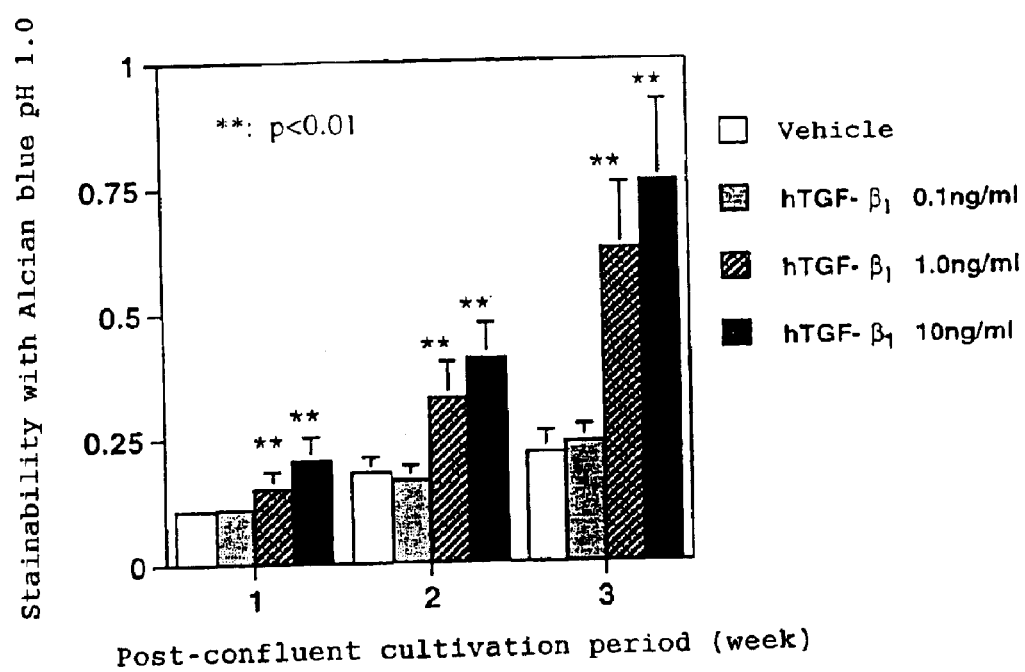
FIG. 9 is a graph showing changes of the stainability of CL-1 cells with Alcian blue (pH 1.0) in the presence of htGF-$\beta_1$.

In order to examine whether or not CL-1 cells can be used as an in vitro screening system for cartilage-inducing materials, effects of hTGF-β, known to have cartilage-inducing ability (J. Biol. Chem. 261, 5693 (1986)) on the stainability of CL-1 cells with Alcian blue (pH 1.0) were examined. Namely, CL-1 cells were cultured on a 24-well plate (CORNING) at a cell density of 2500 cells/cm$^2$ to confluent, at which human transforming growth factor-$\beta_1$ (hTGF-$\beta_1$; AUSTRAL Biologicals) was added at a concentration of 0.1, 1.0 or 10 ng/ml, and cultivation took place for 3 weeks after the start of the addition with the medium being changed every 2 or 3 days. The addition of hTGF-$\beta_1$ was performed for each medium change. After completion of cultivation, cells were fixed in 4% paraformaldehyde (Wako Pure Chemical Industries) and washed with water, then treated with 0.1 N hydrochloric acid (Wako Pure Chemical Industries) for 3 minutes, and then stained overnight with an Alcian blue (pH 1.0) solution (concentration: 1%). After completion of staining, samples were washed with distilled water three times and air-dried. The dried samples were immersed in 300 μl of a 6 M guanidine hydrochloride solution (Wako Pure Chemical Industries) for 3 hours and stirred, after which the absorbance of the guanidine hydrochloride solution at 620 nm was determined. As a result, the stainability with Alcian blue (pH 1.0) increased dose-dependently on hTGF-$\beta_1$ (see FIG. 9).

Figure 10:
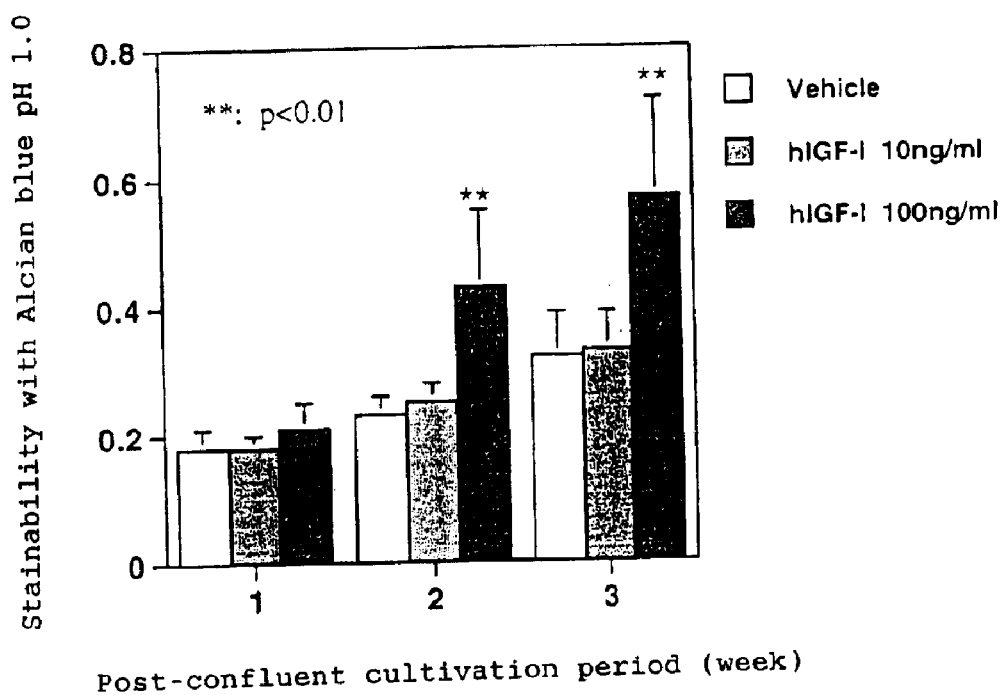
FIG. 10 is a graph showing changes of the stainability of CL-1 cells with Alcian blue (pH 1.0) in the presence of hIGF-I.

Similar tests on human insulin-like growth factor-I (hIGF-I; CHEMICON INTERNATIONAL) known to have an extracellular matrix production-promoting effect on chondrocytes (Ann. Rev. Physiol. 47, 443 (1985)) showed an increase of the stainability with Alcian blue (pH 1.0) at 100 ng/ml (see FIG. 10).

Figure 11:
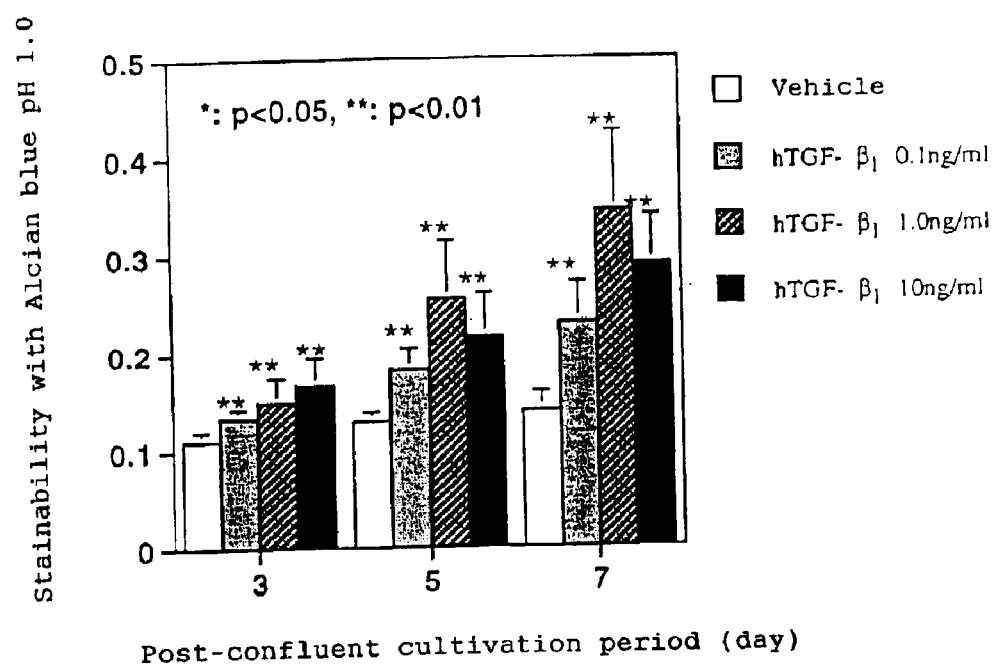
FIG. 11 is a graph showing changes of the stainability of CL-1 cells with Alcian blue (pH 1.0) when hTGF-$\beta_1$ was daily added.
Figure 12:
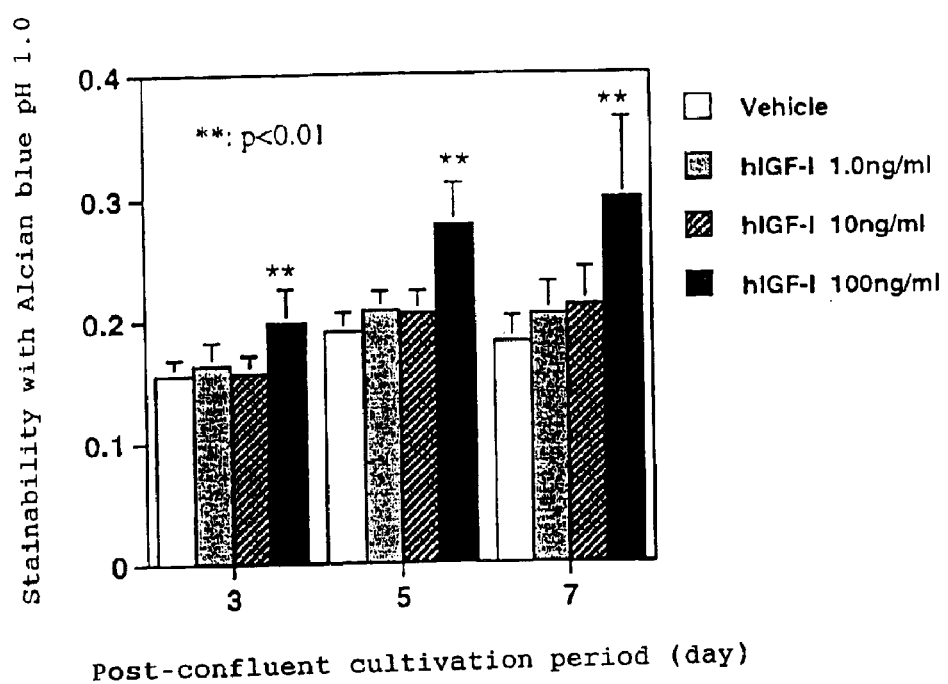
FIG. 12 is a graph showing changes of the stainability of CL-1 cells with Alcian blue (pH 1.0) when hIGF-I was daily added.

Similar results were obtained when hTGF-$\beta_1$ (see FIG. 11) or hIGF-I (see FIG. 12) was daily added for 5 to 7 days after CL-1 cells reached confluency.

Figure 13:
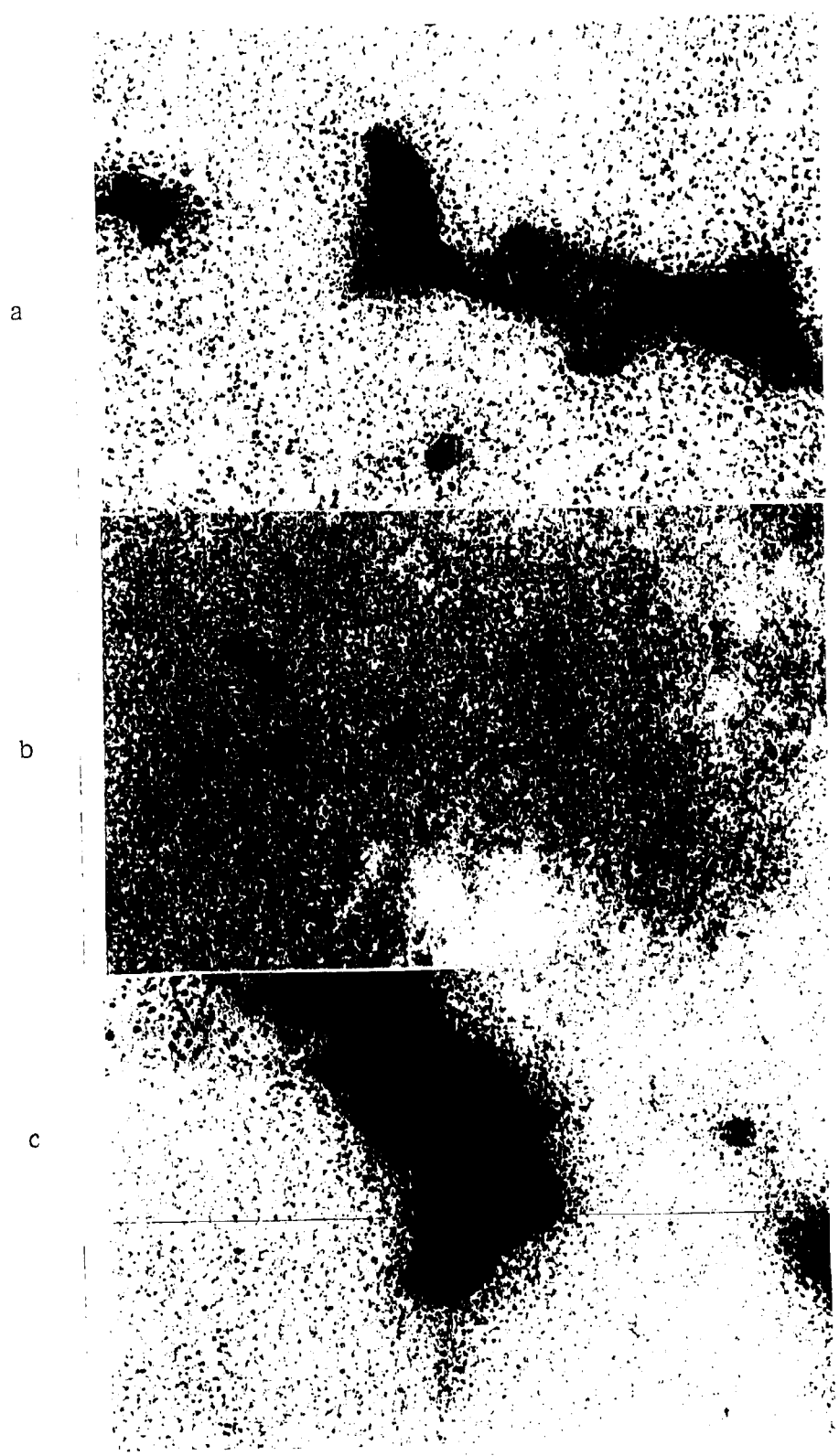
FIG. 13 is a photograph showing changes of Alcian blue-positive nodule formation of CL-1 cells in the presence of hTGF-$\beta_1$ or hIGF-I.

Morphologically, Alcian blue (pH 1.0)-positive nodules clearly increased in the presence of hTGF-$\beta_1$ and hIGF-I as compared with the medium alone (see FIG. 13).

Figure 14:
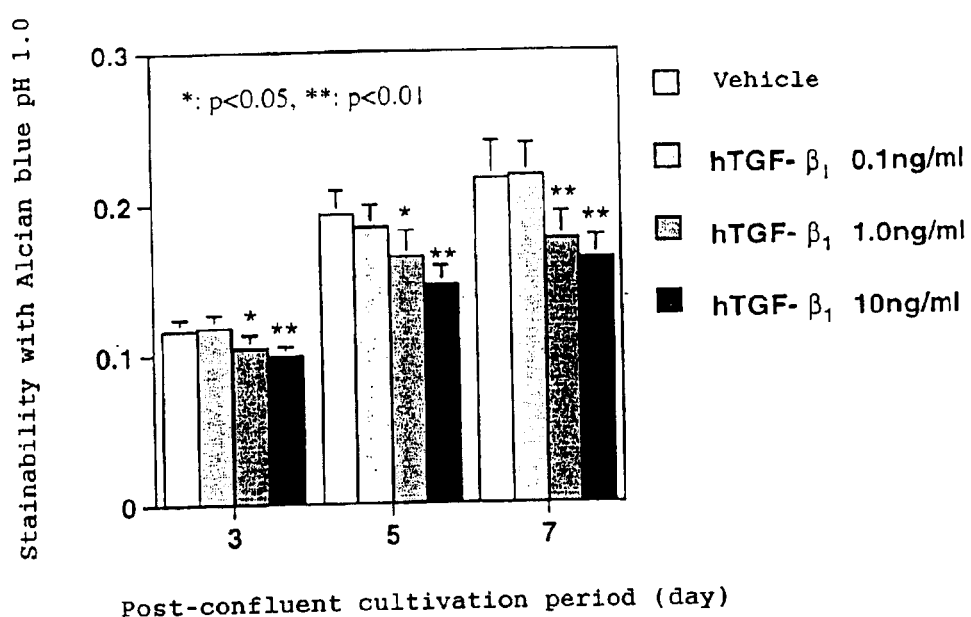
FIG. 14 is a graph showing changes of the stainability of ATDC-5 cell layers with Alcian blue (pH 1.0) when hTGF-$\beta_1$ was daily added.

ATDC-5 cells known to differentiate into chondrocytes in the presence of insulin (Cell Diff. Dev. 30, 109 (1990); available from the Cell Bank of The Institute of Physical and Chemical Research) were also cultured by the same procedure in the presence of 10 μg/ml of insulin and 0.1 to 10 ng/ml of hTGF-$\beta_1$ for 7 days post confluent to examine the stainability with Alcian blue (pH 1.0). As a result, the stainability of ATDC-5 cells with Alcian blue (pH 1.0) dose-dependently decreased by hTGF-$\beta_1$ treatment (see FIG. 14).

These results revealed that CL-1 cells are a useful cell line capable of in vitro evaluating chondrogenesis.

Example 4

Figure 15:
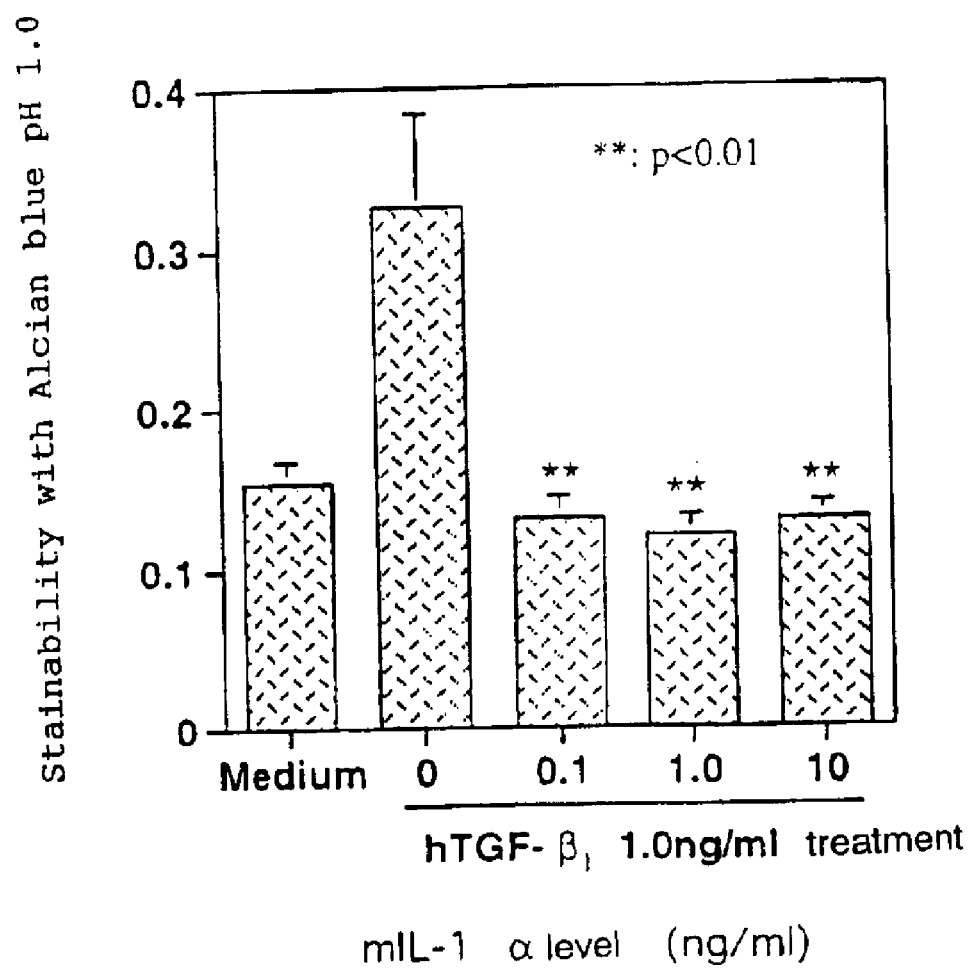
FIG. 15 is a graph showing changes of the stainability of hTGF-$\beta_1$-enhanced CL-1 cell layers with Alcian blue (pH 1.0) in the presence of mIL-1α.
Figure 16:
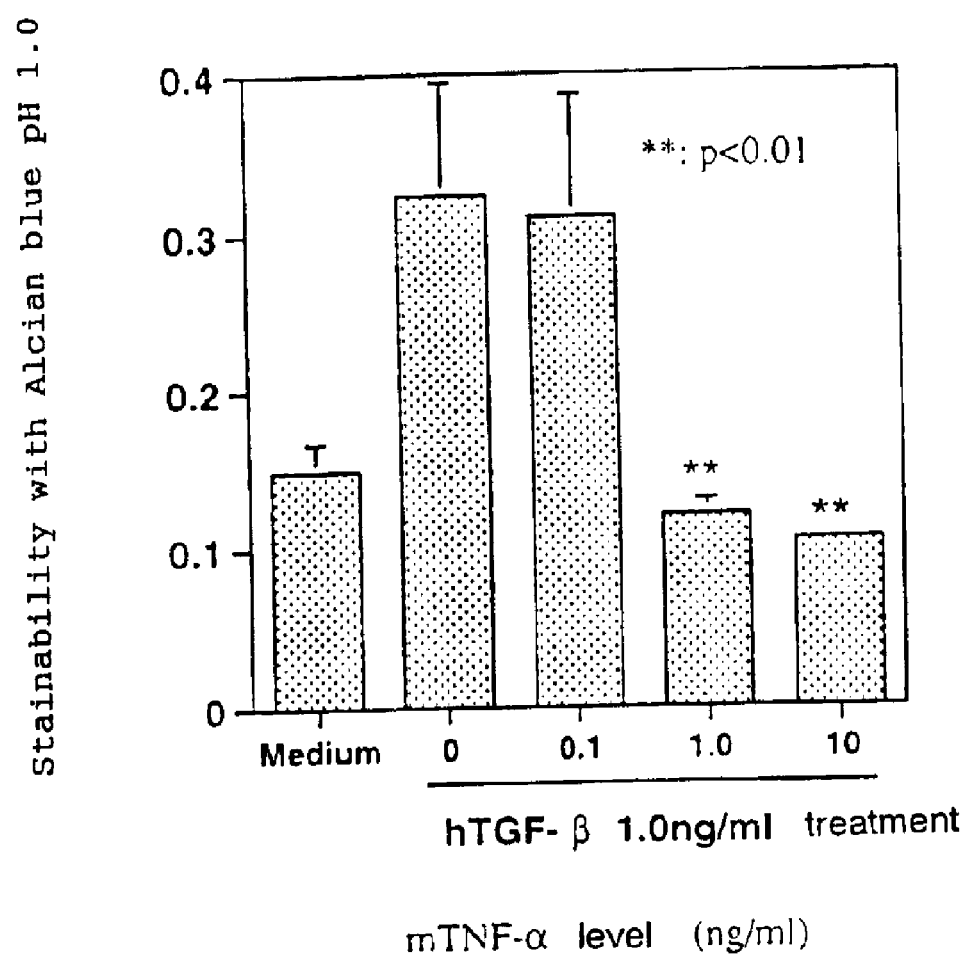
FIG. 16 is a graph showing changes of the stainability of hTGF-$\beta_1$-enhanced CL-1 cell layers with Alcian blue (pH 1.0) in the presence of mTNF-α.
Figure 17:
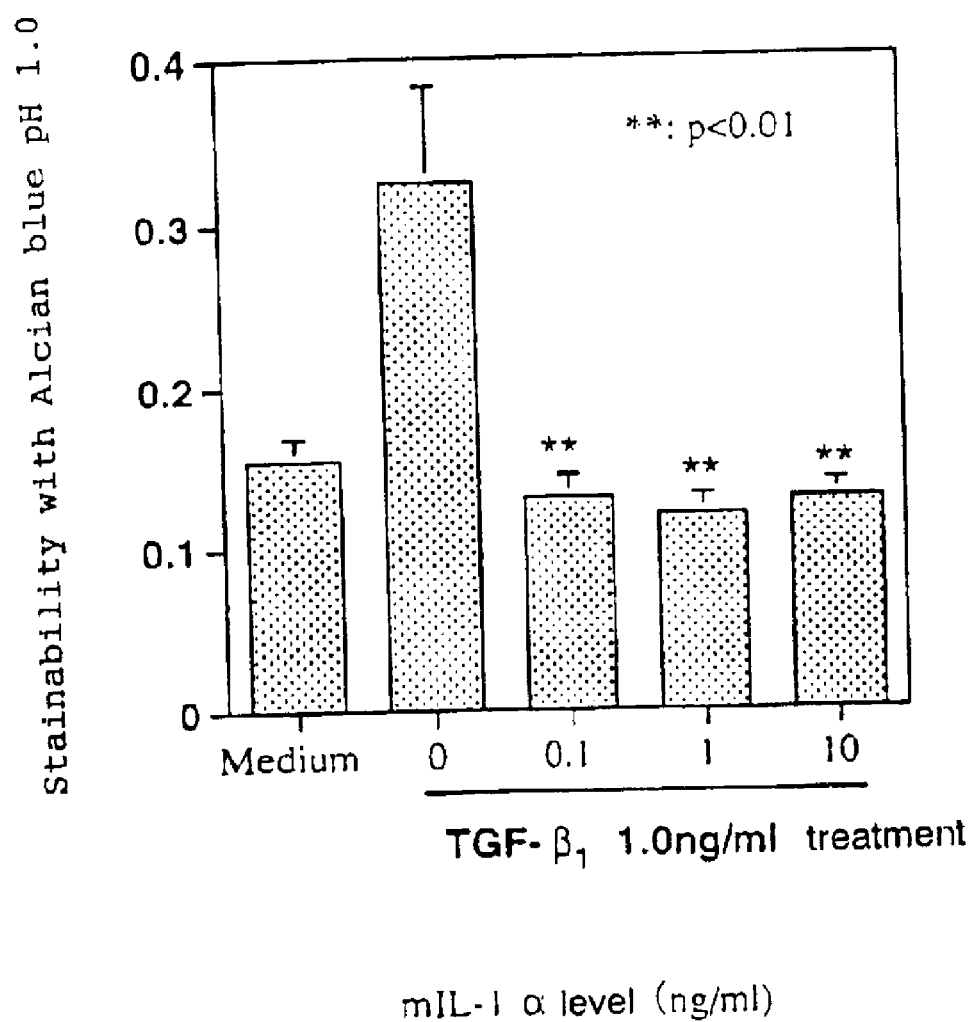
FIG. 17 is a graph showing changes of the stainability of CL-1 cell layers with Alcian blue (pH 1.0) when hTGF-$\beta_1$ and mIL-1α were simultaneously added.
Figure 18:
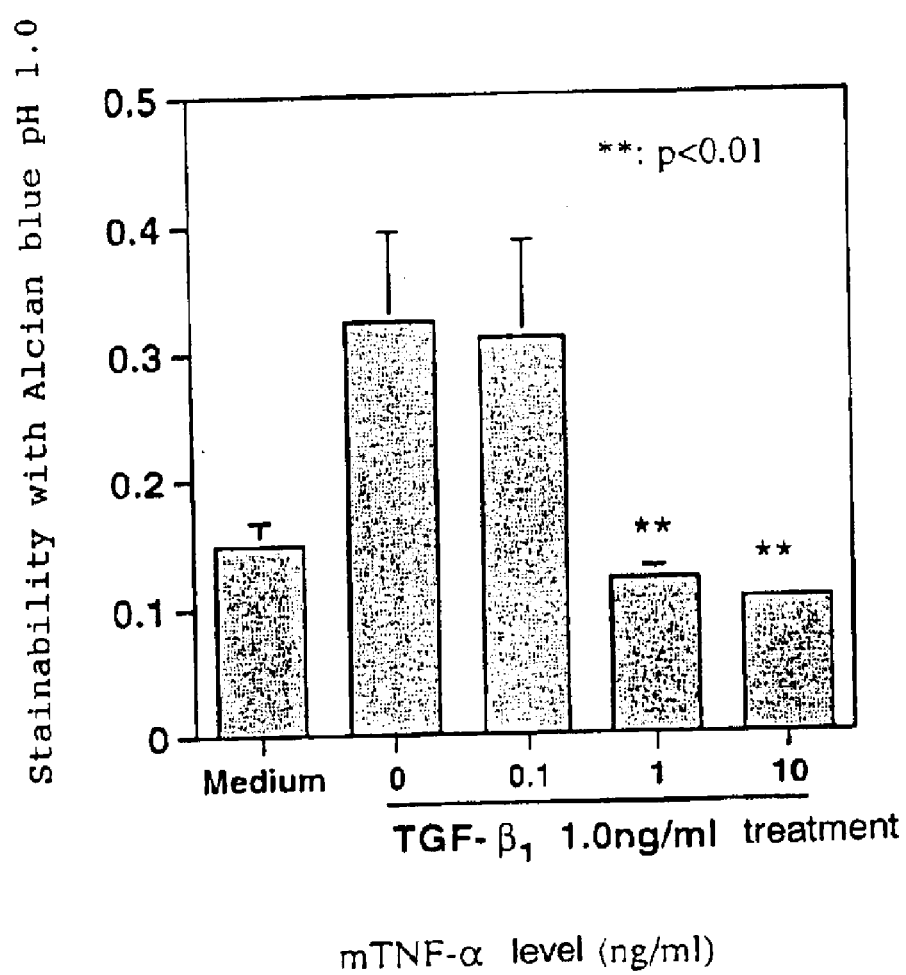
FIG. 18 is a graph showing changes of the stainability of CL-1 cell layers with Alcian blue (pH 1.0) when hTGF-$\beta_1$ and mTNF-α were simultaneously added.

Construction of a System for in Vitro Evaluating Cartilage Destruction Using CL-1 Cells This example relates to an examination about whether or not cartilage-like nodules formed by culturing CL-1 cells in the presence of hTGF-$\beta_1$ are destroyed by inflammatory cytokines IL-1 or TNF-α. CL-1 cells were cultured on a 24-well plate (CORNING) at a cell density of 2500 cells/cm$^2$ to confluent, after which hTGF-$\beta_1$ was daily added to the medium for 5 days at a final concentration of 1.0 ng/ml. Then, mouse interleukin 1α (mIL-1α; R & D systems) and mouse tumor necrosis factor-a (mTNF-α; R & D systems) were daily added to the medium for 5 days at a final concentration of 0.1, 1.0 or 10 ng/ml, and the cells were cultured. Then, the stainability of CL-1 cells with Alcian blue (pH 1.0) was determined as described hereinbefore. As a result, the stainability with Alcian blue (pH 1.0) decreased in the presence of mIL-1α at 0.1 ng/ml or more (see FIG. 15) and mTNF-α at 1.0 ng/ml or more (see FIG. 16). Similar results were obtained when hTGF-$\beta_1$ was added simultaneously with mIL-1α (see FIG. 17) or mTNF-α (see FIG. 18).

These results revealed that CL-1 cells are a useful cell line capable of in vitro evaluating destruction of cartilage tissues by inflammatory cytokines. This indicated that this experimental system can be used to search for inhibitors against cartilage destruction.

Example 5

Figure 19:
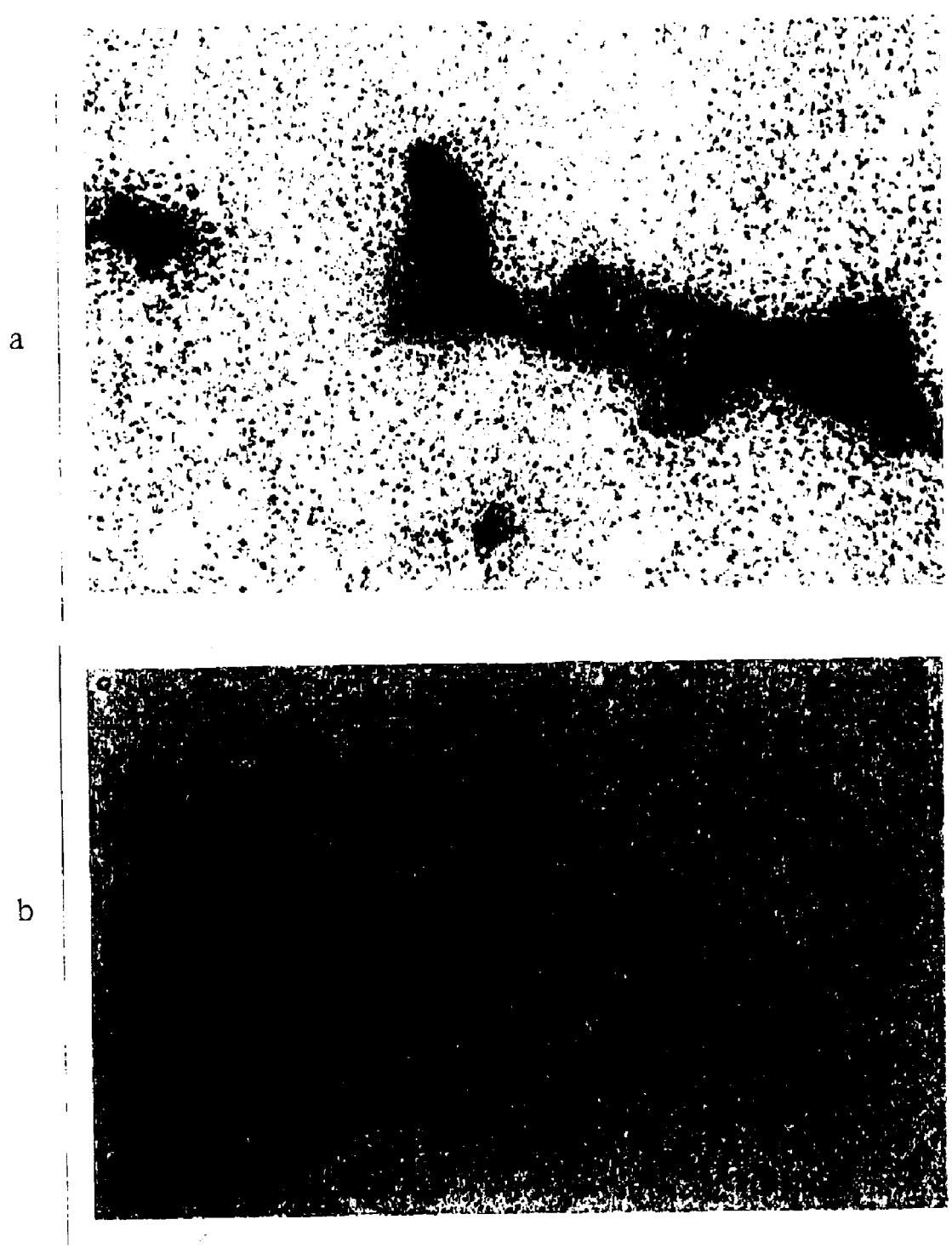
FIG. 19 is a photograph showing inhibition of differentiation of CL-1 cells into adipocytes by 1,25-dihydroxyvitamin $D_3$.

In Vitro Screening for Adipocyte Differentiation-controlling Materials Using CL-1 Cells Influences of 1,25-dihydroxyvitamin $D_3$ known to inhibit conversion of a adipocyte precursor cell line 3T3-L1 into adipocytes (Comp. Biochem. Physiol. 96A, (1990)) on differentiation of CL-1 cells into adipocytes were examined. CL-1 cells were cultured on a 4-well chamber slide (Nunc) at a cell density of 2500 cells/cm$^2$ to confluent, after which 1,25-dihydroxyvitamin $D_3$ was added at a final concentration of $10^{-3}$ M for each medium change. Three weeks after the start of the addition of 1,25-dihydroxyvitamin $D_3$, intracytoplasmic accumulation of Oil red O-positive lipid droplets was observed with a microscope. As a result, 1,25-dihydroxyvitamin $D_3$ remarkably inhibited intracellular accumulation of Oil red O-positive lipid droplets (see FIG. 19).

Similar tests in the presence of hIGF-I known to have a fat synthesis-promoting effect on adipocytes (Ann. Rev. Physiol. 47, 443 (1985)) showed that accumulation of Oil red O-positive lipid droplets in CL-1 cells was promoted as compared with the medium alone (see FIG. 13c).

These results revealed that CL-1 cells are useful as an in vitro evaluation system for materials inhibiting or promoting differentiation from undifferentiated mesenchymal cells into adipocytes.

Example 6

Screening for Chondrocalcification Inhibitors Using CL-1 Cells

Influences of 1,25-dihydroxyvitamin $D_3$ known to suppressively act during calcification of cartilages (Proc. Natl. Acad. Sci. 87, 6522 (1990)) on calcification of CL-1 cells were examined.

Figure 20:
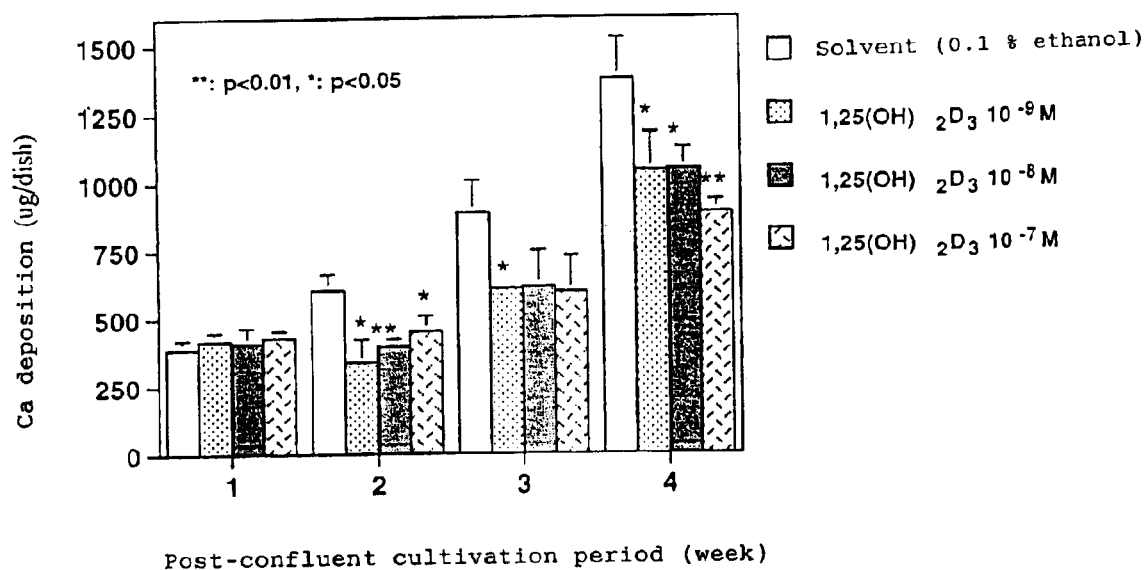
FIG. 20 is a graph showing changes of Ca deposition in CL-1 cell layers in the presence of 1,25-dihydroxyvitamin $D_3$.

CL-1 cells were cultured on a 60-mm dish (CORNING) at a cell density of 2000 cells/cm$^2$. When cells reached to confluent, 1,25-dihydroxyvitamin $D_3$ was added at a final concentration of $10^{-9}$, $10^{-8}$ or $10^{-7}$ M, then samples were weekly collected for 4 weeks post confluent to determine the Ca content with time. Namely, cell layers were washed with Ca-Mg-free PBS three times, then harvested in a crucible with a cell scraper (Nunc), then dried in an incubator at 60° C., then burned overnight in an oven at 800° C., and the remaining ash was dissolved in 500 μl of 6N hydrochloric acid (Wako Pure Chemical Industries). The Ca content in this solution was determined by the O-CPC method (Ca test Wako, available from Wako Pure Chemical Industries) to calculate the Ca deposition per dish. As a result, 1,25-dihydroxyvitamin $D_3$ significantly inhibited an amount of Ca deposition as compared with a solvent control groups on and after 2 weeks post confluent (see FIG. 20). This result revealed that CL-1 cells are a cell line capable of in vitro evaluating materials inhibiting calcification of cartilages.

Example 7

In Vitro Evaluation of the Activity of Promoting Differentiation Into Cartilages Using CL-1 Cells This example relates to an evaluation of the activity of promoting differentiation into cartilages on the basis of the uptake of $^{35}$S-labeled sulfuric acid, as compared with Example 3 which relates to an evaluation of cartilage-inducing potency on the basis of the stainability with Alcian blue.

CL-1 cells were plated on a polystyrene 96-well plate (Wallac) at a cell density of 2000 cells/well, and incubated in (α-MEM (GIBCO) containing 10% inactivated serum (Intergen), 100 U/ml penicillin and 100 μg/ml streptomycin in an incubator at 37° C., 5% $CO_2$, with the medium being changed with a fresh medium 3 times a week to reach confluency. After confluency was confirmed with a microscope, the medium was changed with a fresh medium containing human TGF-$\beta_1$ (AUSTRAL BIOLOGICALS) at a concentration of 0.1, 1.0 or 10 ng/ml and incubation was continued. After 24 hours, $^{35}$S-labeled sulfuric acid (Amersham) was added at 0.5 μCi/well and incubation was continued for further 24 hours. Then, the medium was changed with 200 μl of 0.1 M phosphate buffer (pH 7.4) containing 5% paraformaldehyde (Wako Pure Chemical Industries) and 0.4% cetylpyridinium chloride (Wako Pure Chemical Industries) for fixation at room temperature for 2 hours. After CL-1 cell layers were washed once with the same buffer, 100 μl of a liquid scintillator (Optiphase supermix, available from Wallac) was added to each well followed by stirring, so that the radioactivity of $^{35}$S-labeled sulfuric acid incorporated into CL-1 cell layers was determined by a liquid scintillation counter (Microbeta 1450, available from Wallac).

As a result, human TGF-$\beta_1$ showed a statistically significant increase of the uptake of $^{35}$S-labeled sulfuric acid at 0.1 ng/ml or more as compared with a control containing the medium alone.

Figure 21:
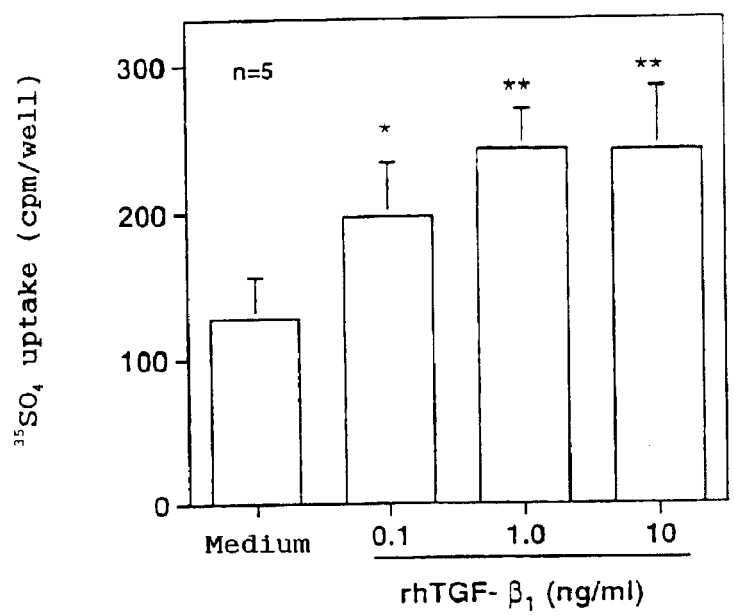
FIG. 21 is a graph showing changes of the uptake of $^{35}$S-labeled sulfuric acid into CL-1 cells in the presence of TGF-$\beta_1$.

The results in the presence of TGF-$\beta_1$ are shown in FIG. 21. As apparent from FIG. 21, the uptake of $^{35}$S-labeled sulfuric acid increased up to about double by addition of TGF-$\beta_1$.

This screening method based on the uptake of $^{35}$S-labeled sulfuric acid can yield results within 2 days after reaching confluency, thus saving time and labor as compared with the method based on the stainability with Alcian blue. The screening method using CL-1 cells provides unprecedented utility, because any system capable of evaluating the activity of a material added after reaching confluency for promoting differentiation into chondrocytes within 2 days has not been reported.

INDUSTRIAL APPLICABILITY

Cell lines of the present invention are novel cell lines derived from normal adult animals and capable of differentiating into chondrocytes and adipocytes. Cell lines of the present invention can be used to screen for cell differentiation-controlling materials, such as materials controlling differentiation into chondrocytes and adipocytes, materials inhibiting destruction of cartilage tissues or materials controlling calcification of chondrocytes.

Materials obtained by screening methods using cell lines of the present invention can be used as useful therapeutic agents taking advantage of their characteristics in the field of repair or reconstruction of articular cartilages, ear or nose, maintenance of articular functions by inhibition of calcification of articular cartilages, inhibition of destruction of articular cartilages caused by inflammation of joint, or therapy of obesity or the like.

The whole content of Japanese Patent Application No. 70556/97, on which the priority claim of the present application is based, is incorporated herein as reference.

SEQUENCE LISTING

SEQ ID NO:1
Length of Sequence: 19
Type of Sequence: nucleic acid
Number of Strand: single
Topology: linear
Type of Sequence: other type, synthetic DNA
Feature of Sequence:
   KEY indicating Feature: unsure
   Location: 1 . . . 19
   Method of Determining Feature: E
Sequence
ACACAATCCA TTGCGAACC 19
SEQ ID NO:2
Length of Sequence: 20
Type of Sequence: nucleic acid
Number of Strand: single
Topology: linear
Type of Sequence: other type, synthetic DNA
Feature of Sequence:
   KEY indicating Feature: unsure
   Location: 1 . . . 20
   Method of Determining Feature: E
Sequence AGATAGTTCC TGTCTCCGCC 20
SEQ ID NO:3
Length of Sequence: 21
Type of Sequence: nucleic acid
Number of Strand: single
Topology: linear
Type of Sequence: other type, synthetic DNA
Feature of Sequence:
   KEY indicating Feature: unsure
   Location: 1 . . . 21
   Method of Determining Feature: E
Sequence
CAGCTGGCAT AGCAACTAAG G 21
SEQ ID NO:4
Length of Sequence: 20
Type of Sequence: nucleic acid
Number of Strand: single
Topology: linear
Type of Sequence: other type, synthetic DNA
Feature of Sequence:
   KEY indicating Feature: unsure
   Location: 1 . . . 20
   Method of Determining Feature: E
Sequence
GTGGTTAGCA CTGACAAGCG 20
SEQ ID NO:5
Length of Sequence: 20
Type of Sequence: nucleic acid
Number of Strand: single
Topology: linear
Type of Sequence: other type, synthetic DNA
Feature of Sequence:
   KEY indicating Feature: unsure
   Location: 1 . . . 20
   Method of Determining Feature: E
Sequence
TGTTCAGTGG AACAGCAACC 20
SEQ ID NO:6
Length of Sequence: 22
Type of Sequence: nucleic acid
Number of Strand: single
Topology: linear
Type of Sequence: other type, synthetic DNA
Feature of Sequence:
   KEY indicating Feature: unsure
   Location: 1 . . . 22
   Method of Determining Feature: E
Sequence
AGATTGTTCA CTGACGTCCA CC 22
SEQ ID NO:7
Length of Sequence: 20
Type of Sequence: nucleic acid
Number of Strand: single
Topology: linear
Type of Sequence: other type, synthetic DNA
Feature of Sequence:
   KEY indicating Feature: unsure
   Location: 1 . . . 20
   Method of Determining Feature: E
Sequence CTGATGCACT GCCTATGAGC 20
SEQ ID NO:8
Length of Sequence: 20
Type of Sequence: nucleic acid
Number of Strand: single Topology: linear
Type of Sequence: other type, synthetic DNA
Feature of Sequence:
  KEY indicating Feature: unsure
  Location: 1 . . . 20
  Method of Determining Feature: E
Sequence
CATGGGCCT GTTGTAGAGC 20

What is claimed is:

1. The cell line which bears accession No. FERM BP-5823.

2. A method for screening for a cell differentiation-controlling material, comprising:

contacting a compound or a mixture of compounds with the cell line of claim 1 to screen for a cell differentiation-controlling material; and determining the capability of the compound or the mixture of compounds to induce differentiation of the cell line.

3. The screening method of claim 2, wherein the material screened for is a gene.

4. The method of claim 2, wherein the cell differentiation-controlling material is a material controlling differentiation into chondrocytes or adipocytes, a material controlling destruction of cartilage tissues or a material controlling calcification of chondrocytes.

5. A kit for screening for a cell differentiation-controlling material, comprising the cell line of claim 1 and a reagent for detecting changes of properties of the cell line which may be caused by the action of a candidate cell differentiation-controlling material to be screened.

6. A kit of claim 5, wherein the cell differentiation-controlling material is a material controlling differentiation into chondrocytes or adipocytes, a material controlling destruction of cartilage tissues or a material controlling calcification of chondrocytes.

* * * * *